(12) United States Patent
Domash

(10) Patent No.: US 8,048,047 B2
(45) Date of Patent: Nov. 1, 2011

(54) SURGICAL CASSETTE WITH IMPROVED AIR FILTERING

(75) Inventor: David M. Domash, Irvine, CA (US)

(73) Assignee: Novartis AG, Basel (CH)

( * ) Notice: Subject to any disclaimer, the term of this patent is extended or adjusted under 35 U.S.C. 154(b) by 171 days.

(21) Appl. No.: 11/473,428

(22) Filed: Jun. 23, 2006

(65) Prior Publication Data

US 2008/0125694 A1 May 29, 2008

(51) Int. Cl.
*A61M 1/00* (2006.01)
(52) U.S. Cl. .......................... 604/319; 604/35
(58) Field of Classification Search ............... 604/131, 604/190, 233–235, 519, 35, 319; 417/477.2
See application file for complete search history.

(56) References Cited

U.S. PATENT DOCUMENTS

| | | | |
|---|---|---|---|
| 3,520,416 A * | 7/1970 | Keedwell | 210/490 |
| 4,453,927 A * | 6/1984 | Sinko | 604/513 |
| 4,493,695 A * | 1/1985 | Cook | 604/27 |
| 4,704,255 A * | 11/1987 | Jolley | 422/101 |
| 4,758,238 A * | 7/1988 | Sundblom et al. | 604/319 |
| 5,106,366 A | 4/1992 | Steppe | |
| 5,267,956 A | 12/1993 | Beuchat | |
| 5,364,342 A | 11/1994 | Beuchat et al. | |
| 5,588,815 A | 12/1996 | Zaleski, II | |
| 6,261,283 B1 | 7/2001 | Morgan et al. | |
| 6,293,926 B1 | 9/2001 | Sorensen et al. | |
| 6,561,999 B1 | 5/2003 | Nazarifar et al. | |
| 6,740,074 B2 | 5/2004 | Morgan et al. | |
| 6,902,542 B2 | 6/2005 | Gordon | |
| 6,962,488 B2 | 11/2005 | Davis et al. | |
| 7,070,578 B2 | 7/2006 | Leukanech et al. | |
| 2003/0209455 A1 | 11/2003 | Pynson et al. | |
| 2003/0225363 A1 | 12/2003 | Gordon et al. | |

FOREIGN PATENT DOCUMENTS

| | | |
|---|---|---|
| DE | 92 03 039 | 5/1992 |
| EP | 0378296 A2 | 7/1990 |
| RU | 2116112 C1 | 7/1998 |
| WO | WO 2007/149637 A2 | 12/2007 |
| WO | WO 2007/149637 A3 | 12/2007 |

OTHER PUBLICATIONS

Osinski, Bradley James, Written Opinion of the International Searching Authority, International Application No. PCT/US2007/068087, Jun. 2, 2008, 3 pages.
Abstract of RU 2312643 C1, Published Dec. 20, 2007.

* cited by examiner

*Primary Examiner* — Kevin C Sirmons
*Assistant Examiner* — Bradley J Osinski

(57) ABSTRACT

A surgical cassette having a filter media sealingly disposed between a first rigid surface and a second rigid surface in a filter chamber of the cassette housing provides improved air filtering for the cassette.

13 Claims, 4 Drawing Sheets

SURGICAL CASSETTE WITH IMPROVED AIR FILTERING

FIELD OF THE INVENTION

The present invention generally pertains to microsurgical systems and more particularly to surgical cassettes used in such microsurgical systems.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. A surgical cassette, which is fluidly coupled to both the probe and a surgical system or console, manages the fluids infused into the eye and aspirated from the surgical site.

During ophthalmic surgery, pressurized air may be used for a variety of functions. Certain of these functions require sterile air to pressurize a surgical irrigating fluid that is infused into the eye. Conventionally, such pressurized air is provided by the surgical system to which a surgical cassette is fluidly coupled. To sterilize the pressurized air, standard medical grade air filters have been disposed within such surgical systems on pneumatic lines that are fluidly coupled to the surgical cassette when the cassette is disposed within the surgical system. Such standard air filters include a hydrophobic, micro-bacterial filter media installed within a plastic filter housing. The cost of the filter media installed in the housing is approximately ten times the cost of the filter media itself. Hydrophobic, micro-bacterial filter media have also been disposed directly into surgical cassettes between a portion of the rigid housing of the cassette and an elastomeric media that acts as an interface between the cassette and moving parts of the surgical system. However, such designs require gaskets or other components to effectively seal the filter media to the cassette.

Accordingly, a need continues to exist for improved air filter within a surgical cassette.

SUMMARY OF THE INVENTION

The present invention is a surgical cassette with an improved air filter. In one aspect, the cassette includes a cassette housing having a filter chamber with a first rigid surface, a second rigid surface, and a port for providing pressurized air to the chamber. A filter media is disposed within the chamber between the first rigid surface and the second rigid surface. The filter media is thermally sealed to either the first rigid surface or the second rigid surface.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
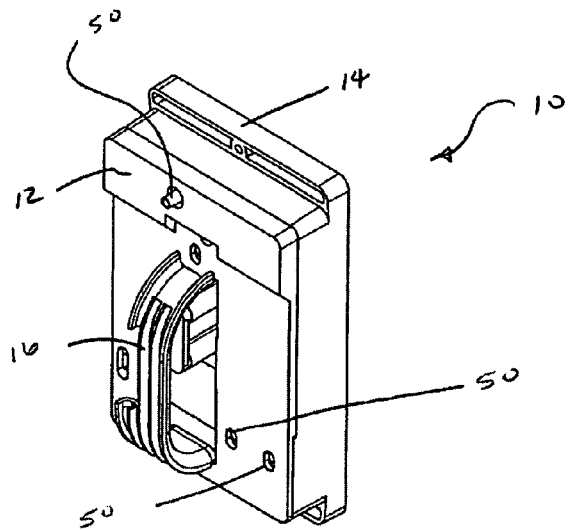
FIG. 1 is a front, perspective view of a surgical cassette according to a preferred embodiment of the present invention.
Figure 2:
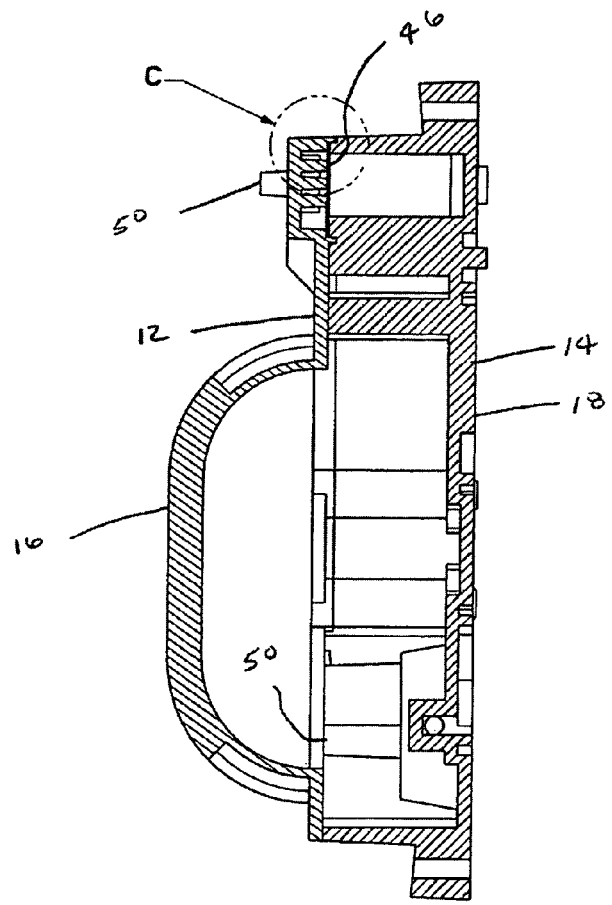
FIG. 2 is a side, sectional view of the surgical cassette of FIG. 1.

The preferred embodiments of the present invention and their advantages are best understood by referring to FIGS. 1-7 of the drawings, like numerals being used for like and corresponding parts of the various drawings. As shown in the Figures, ophthalmic surgical cassette 10 preferably includes a housing 11 having a cover 12 and a body 14. Both cover 12 and body 14 are preferably made of rigid plastic. Cover 12 preferably includes a handle 16 to facilitate disposal of cassette 10 into an ophthalmic surgical system (not shown). A rear wall 18 of body 14 is for operatively coupling with a surgical system. Although cassette 10 is described herein as an ophthalmic surgical cassette, cassette 10 may alternatively be utilized in connection with any surgical or medical system requiring fluid management.

Figure 3:
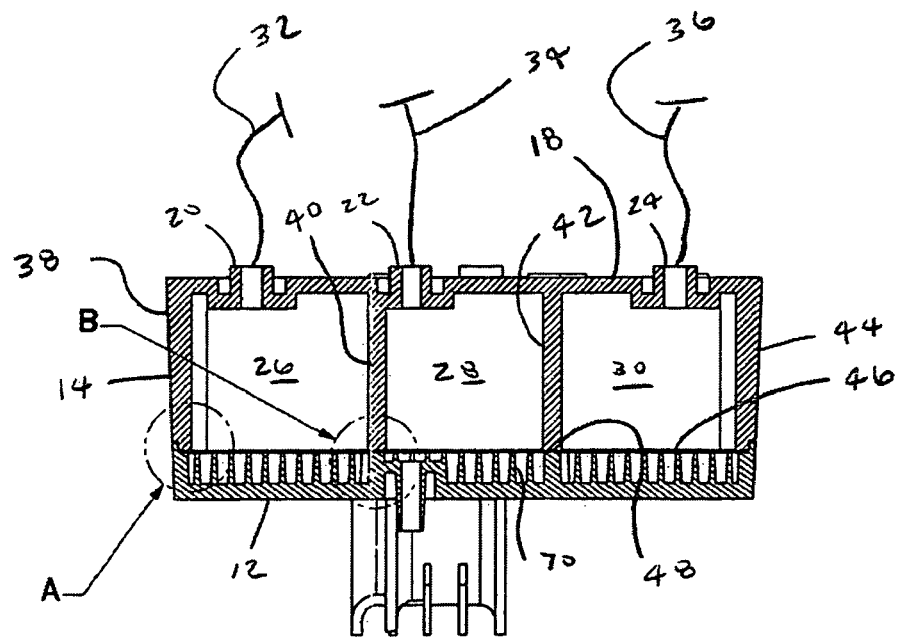
FIG. 3 is a top, sectional view of the surgical cassette of FIG. 1.

As shown best in FIG. 3, rear wall 18 preferably includes ports 20, 22, and 24 that are fluidly coupled to chambers 26, 28, and 30, respectively. Ports 20, 22, and 24 are for fluidly coupling to fluid lines 32, 34, and 36 disposed in the surgical system and that provide pressurized air to chambers 26, 28, and 30. Chamber 26 is preferably formed by rear wall 18, side wall 38, and internal wall 40 of body 14. Chamber 28 is preferably formed by rear wall 18, internal wall 40, and internal wall 42 of body 14. Chamber 30 is preferably formed by rear wall 18, internal wall 42, and side wall 44 of body 14. A filter media 46 is disposed along a front surface 48 of walls 38, 40, 42, and 44 between body 14 and cover 12. Filter media 46 is preferably thermally sealed to body 14 along front surface 48. Filter media 46 is preferably a conventional hydrophobic, micro-bacterial filter that is typically used in standard medical grade filters. A preferred filter media is the VERSAPOR® membrane filter (0.8 micron) available from Pall Corporation. Cassette 10 preferably includes one or more fluid lines, passageways, and/or ports 50 fluidly coupled to each of chambers 26, 28, and 30 for providing pressurized air to other portions of cassette 10 and/or surgical handpieces (not shown) fluidly coupled to cassette 10.

Figure 4:
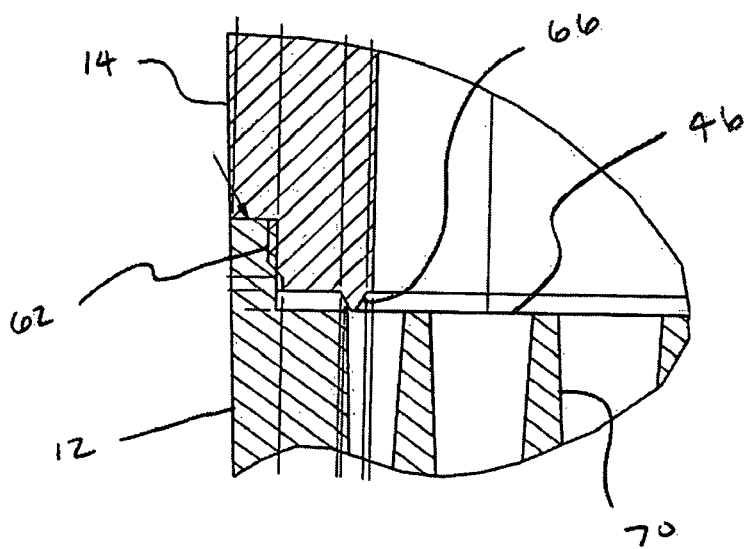
FIG. 4 is an enlarged, fragmentary, sectional view of the area shown in circle A in FIG. 3.
Figure 5:
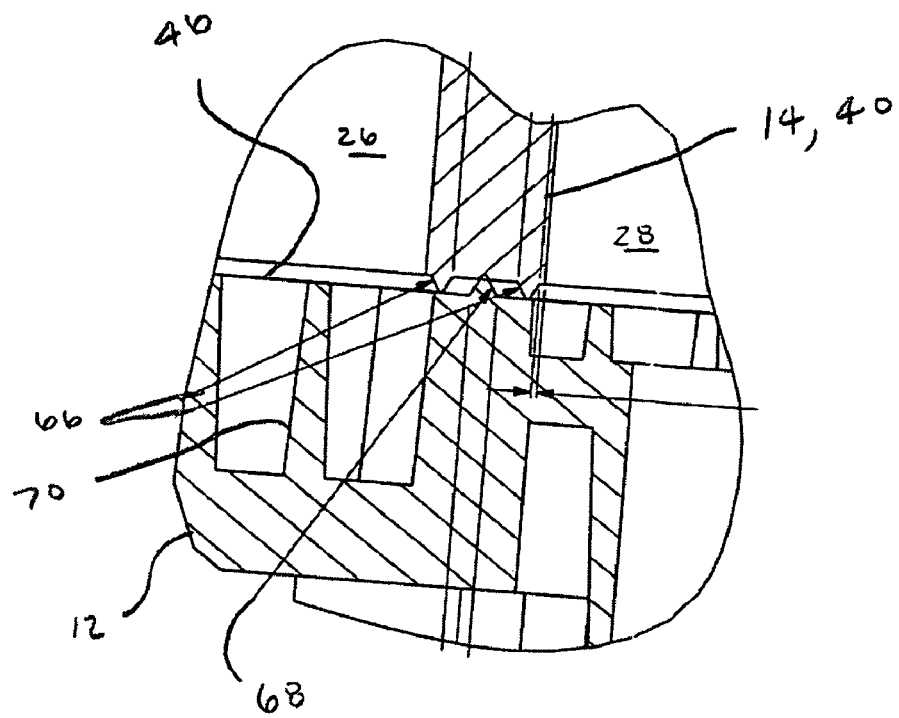
FIG. 5 is an enlarged, fragmentary, sectional view of the area shown in circle B in FIG. 3.
Figure 6:
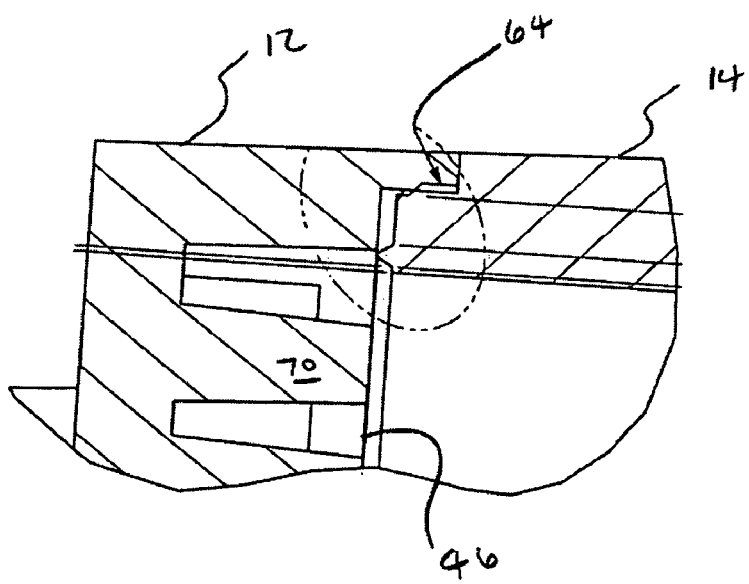
FIG. 6 is an enlarged, fragmentary, sectional view of the area shown in circle C in FIG. 2.
Figure 7:
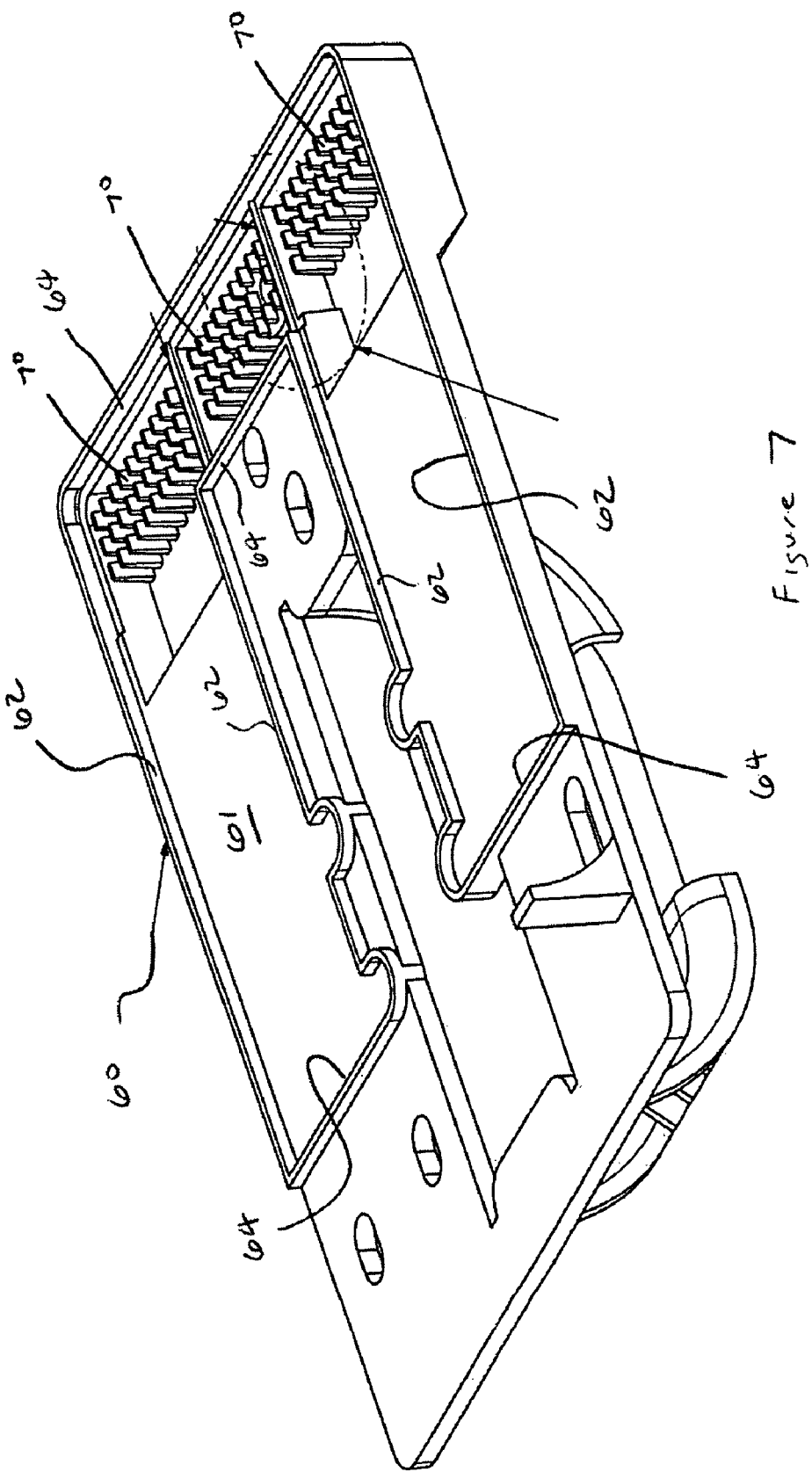
FIG. 7 is an enlarged, rear, perspective view of the cover of the surgical cassette of FIG. 1.

As shown best in FIGS. 4, 6, and 7, cover 12 preferably has a lip 60 disposed on its rear surface 61. Lip 60 enables cover 12 and body 14 to be fluidly sealed together, preferably via a shear weld along surfaces 62 and 64. As shown best in FIGS. 4, 5, and 6, body 14 preferably has raised sealing surfaces 66 that interface with filter media 46 to seal media 46 between body 14 and cover 12. Cover 12 preferably has raised sealing surfaces 68 for interfacing with filter media 46 and internal walls 40 and 42 of body 14 to seal filter chamber 26 from filter chamber 28 and filter chamber 30 from filter chamber 28. Cover 12 also preferably has a plurality of sealing force directors 70 for interfacing with filter media 46 to seal media 46 between body 14 and cover 12.

From the above, it may be appreciated that the present invention provides improved air filtering in a surgical cassette. The present invention eliminates the need for filter housings used in standard medical grade air filters, substantially decreases the cost of air filtering in a surgical cassette, enables the production of multiple filter chambers at the same time, and requires no gaskets or other components to seal the filter media to the cassette.

The present invention is illustrated herein by example, and various modifications may be made by a person of ordinary skill in the art. For example, while the present invention is described above with filter media 46 being sealed between cover 12 and body 14 of cassette 10, filter media 46 may be sealed between any two rigid components of cassette 10, such as a pinch plate and a body. As another example, while the present invention is described above with filter media 46 being thermally sealed to only body 14, media 46 may also be thermally sealed to cover 12.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A surgical cassette, comprising:
   a body, comprising:
      a rear wall;
      a back side wall extending from the rear wall;
      an internal wall extending from the rear wall to separate a first chamber and a second chamber;
      a first entry port extending through the rear wall to supply fluid to the first chamber;
      a second entry port extending through the rear wall to supply fluid to the second chamber;
   a cover coupled to the body, wherein the cover comprises:
      a first exit port extending through the cover to receive fluid from the first chamber;
      a second exit port extending through the cover to receive fluid from the second chamber;
      a plurality of sealing force directors; wherein the plurality of sealing force directors comprises an array of at least three sealing force directors in the first chamber and a separate array of at least three sealing force directors in the second chamber;
   a single filter media secured between the cover and the body through interfacing raised sealing surfaces between the body and cover, wherein the single filter media extends through the first chamber and the second chamber to filter air traveling through the first chamber and the second chamber, and wherein at least a subset of the raised sealing surfaces have a triangular cross-section with an apex of the triangular cross-section directly contacting the filter media to seal the single filter media in position between the body and cover such that the single filter media is positioned directly over the plurality of sealing force directors;
   wherein the first chamber includes at least the rear wall, the cover on an opposing side of the first chamber as the rear wall, the back side wall, and the internal wall;
   wherein the second chamber includes at least the rear wall, the cover on an opposing side of the second chamber as the rear wall, the back side wall, and the internal wall.

2. The surgical cassette of claim 1, wherein several of the raised sealing surfaces extend from the internal wall.

3. The surgical cassette of claim 1, wherein said filter media is thermally sealed to both the cover and the body.

4. The surgical cassette of claim 1, wherein said filter media is a hydrophobic, micro-bacterial filter media.

5. The surgical cassette of claim 1,
   wherein the body further comprises a third chamber;
   wherein the single filter media is disposed across the first, second, and third chambers.

6. The surgical cassette of claim 1, wherein the first port and the second port are coupled to different fluid lines.

7. The surgical cassette of claim 1, wherein the surgical cassette is an ophthalmic surgical cassette.

8. A surgical cassette, comprising:
   a body, comprising:
      a rear wall;
      a back side wall extending from the rear wall;
      an internal wall extending from the rear wall to separate a first chamber and a second chamber;
      a first entry port extending through the rear wall to supply fluid to the first chamber;
      a second entry port extending through the rear wall to supply fluid to the second chamber;
   a cover coupled to the body, wherein the cover comprises:
      a first exit port extending through the cover to receive fluid from the first chamber;
      a second exit port extending through the cover to receive fluid from the second chamber;
      a plurality of sealing force directors; wherein the plurality of sealing force directors comprises an array of at least three sealing force directors in the first chamber and a separate array of at least three sealing force directors in the second chamber;
   a single filter media secured between the cover and the body through interfacing raised sealing surfaces between the body and cover, wherein the single filter media extends through the first chamber and the second chamber to filter air traveling through the first chamber and the second chamber, and wherein the single filter media is thermally sealed between the internal wall and the cover and is further secured between the cover and the body through interaction with at least a subset of raised sealing surfaces, wherein the raised sealing surfaces have a triangular cross-section with an apex of the triangular cross-section directly contacting the filter media;
   wherein the first chamber includes at least the rear wall, the cover on an opposing side of the first chamber as the rear wall, the back side wall, and the internal wall;
   wherein the second chamber includes at least the rear wall, the cover on an opposing side of the second chamber as the rear wall, the back side wall, and the internal wall.

9. The surgical cassette of claim 8, wherein several of the raised sealing surfaces extend from the internal wall.

10. The surgical cassette of claim 8, wherein said filter media is a hydrophobic, micro-bacterial filter media.

11. The surgical cassette of claim 8,
    wherein the body further comprises a third chamber;
    wherein the single filter media is disposed across the first, second, and third chambers.

12. The surgical cassette of claim 8, wherein the first port and the second port are coupled to different fluid lines.

13. The surgical cassette of claim 8, wherein the surgical cassette is an ophthalmic surgical cassette.

* * * * *